United States Patent [19]

Sabesan

[11] Patent Number: 5,288,859
[45] Date of Patent: Feb. 22, 1994

[54] PROCESS FOR THE PREPARATION OF GLYCOSYL AZIDES

[75] Inventor: Subramaniam Sabesan, Wilmington, Del.

[73] Assignee: E. I. Du Pont de Nemours and Company, Wilmington, Del.

[21] Appl. No.: 644,390

[22] Filed: Jan. 22, 1991

[51] Int. Cl.$^5$ .................. C07H 5/04; C07H 11/04; C07H 13/02
[52] U.S. Cl. .................. 536/124; 536/18.7; 536/120; 536/117
[58] Field of Search .................. 536/22, 124, 18.7

[56] References Cited

U.S. PATENT DOCUMENTS

| | | | |
|---|---|---|---|
| 4,659,810 | 4/1987 | Thiem et al. | 536/22 |
| 4,785,084 | 11/1988 | Warren et al. | 536/17.9 |
| 5,095,123 | 3/1992 | Sabesan | 549/222 |

OTHER PUBLICATIONS

Kunz, H. (1987) Angew. Chem. Int. Ed. Engl. 26: 294–308.

Primary Examiner—Johnnie R. Brown
Assistant Examiner—Gary L. Kunz

[57] ABSTRACT

A process for stereospecific preparation of glycosyl azides by reacting a metal azide with a glycosyl phosphate triester having the phosphate group cis to the adjacent C-2 substituent is disclosed.

10 Claims, No Drawings

PROCESS FOR THE PREPARATION OF GLYCOSYL AZIDES

FIELD OF THE INVENTION

This invention relates to a stereospecific process for the preparation of glycosyl azides which are key intermediates in the synthesis of glycosyl amino acids.

BACKGROUND OF THE INVENTION

Glycoproteins play an important role in biological recognition processes on cell membranes as occur in immune reactions and infection processes. Well-defined model compounds which correspond to characteristic structural elements of the glycoproteins that participate in these recognition processes are required to carry out studies of these processes. Glycopeptides, which are partial structures of the connecting regions of glycoproteins and contain glycosidic bonds between the carbohydrate and peptide parts, are molecules capable of serving as such model compounds. Glycosyl azides are key intermediates in the synthesis of glycosyl amino acids which themselves are useful for the synthesis of glycopeptides.

Glycosyl azides are conventionally prepared by the displacement of the corresponding glycosyl halide with azide ion. See H. Kunz, Angew. Chem. Int. Ed. Engl. 26 (1987) 294–308 for a number of references disclosing variations of this method. Although this method is a useful one, it has some limitations. For example, the commonly available glycosyl halides have the anomeric halide atom axial to the pyranose ring due to the anomeric effect, and so, preparation of glycosyl azides via this method gives products with the azido group in the equatorial position ($\beta$-glycosyl azides) irrespective of the sugars used. A further limitation of this method is that glycosyl halide reactants, especially those with an acetamido group next to the anomeric center, are unstable.

There is a need for a stereospecific process for the preparation of glycosyl azides which overcomes the limitations of the described conventional method. Such a process should be capable of providing glycosyl azides with the azide group either axial or equatorial to the pyranose ring. Furthermore, the starting materials utilized by such a method should be stable. The object of this invention is to provide such a process wherein 1,2-cis-glycosyl phosphates can be converted to 1,2-trans-glycosyl azides.

SUMMARY OF THE INVENTION

The present invention provides a process for the stereospecific preparation of glycosyl azides comprising reacting a metal azide with a glycosyl phosphate triester having the phosphate group cis to the adjacent C-2 substituent. The reaction proceeds with inversion of configuration at the reaction site yielding 1,2-trans-glycosyl azides.

DETAILED DESCRIPTION OF THE INVENTION

Glycosyl azides which can be prepared by the process of the present invention are represented by the following formulae:

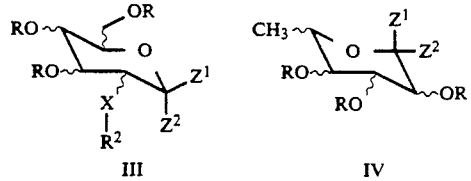

wherein:
R is alkyl, aryl, aralkyl, acyl or aroyl;
X is oxygen and $R^2$ is alkyl, aryl, aralkyl, acyl or aroyl, or X is NH and $R^2$ is acyl, aroyl or alkylcarbamyl;
one of $Z^1$ or $Z^2$ is $N_3$, and the other is H.

In preferred compounds of Formula III or IV,
R is benzyl, acetyl or benzoyl;
X is oxygen and $R^2$ is benzyl, acetyl or benzoyl, or X is NH and $R^2$ is acetyl;
one of $Z^1$ or $Z^2$ is $N_3$, and the other is H.

The alkyl groups may contain from 1–12 carbon atoms; the acyl group may contain from 1–17 carbon atoms; the aralkyl group may be benzyl or diphenylmethyl; and the aryl group of the aroyl group may be phenyl or a phenyl substituted with at least one alkyl, halogen or methoxy group.

Compounds which serve as starting materials for the process of this invention may be represented by the following formulae:

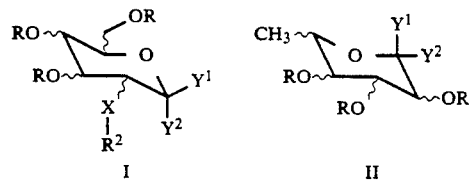

wherein:
R is alkyl, aryl, aralkyl, acyl or aroyl;
X is oxygen and $R^2$ is alkyl, aryl, aralkyl, acyl or aroyl, or X is NH and $R^2$ is acyl, aroyl or alkylcarbamyl;
one of $Y^1$ or $Y^2$ is

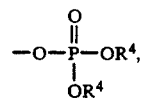

and the other is H; and
$R^4$ is aryl.

Preferred starting materials are compounds of Formula I or II wherein:
R is benzyl, acetyl or benzoyl;
X is oxygen and $R^2$ is benzyl, acetyl or benzoyl, or X is NH and $R^2$ is acetyl;
one of $Y^1$ or $Y^2$ is

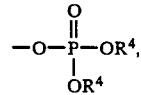

and the other is H; and
$R^4$ is phenyl.

The glycosyl phosphate triester starting materials of Formula I or II are easily prepared by reacting an anomeric mixture of a hexopyranose compound with 4-N,N-dimethylaminopyridine, followed by the addition of diphenyl chlorophosphate. Suitable hexopyranose compounds are those of above Formula I or II wherein one of $Y^1$ or $Y^2$ is OH and the other is H. The reaction is carried out at from about $-30°$ C. to about $25°$ C., preferably from about $0°$ C. to about $25°$ C. in a halogenated hydrocarbon solvent at ambient pressure in an inert atmosphere such as nitrogen or argon. The mole ratio of hexopyranose to either 4-N,N-dimethylaminopyridine or diphenyl chlorophosphate used is about 1:1 to 1:3 when X is oxygen, or a minimum 1:10 hexopyranose to diphenyl chlorophosphate and a minimum 1:20 hexopyranose to 4-N,N-dimethylaminopyridine when X is NH.

In the process of the present invention a glycosyl phosphate triester is reacted with an azide ion to yield the corresponding glycosyl azide. The reaction is stereospecific, proceeding with inversion of configuration at the reaction site; thus, reaction of an α-glycosyl phosphate triester with azide ion yields a β-glycosyl azide, and reaction of a β-glycosyl phosphate triester yields an α-glycosyl azide, as shown in Reaction Scheme I.

Scheme I

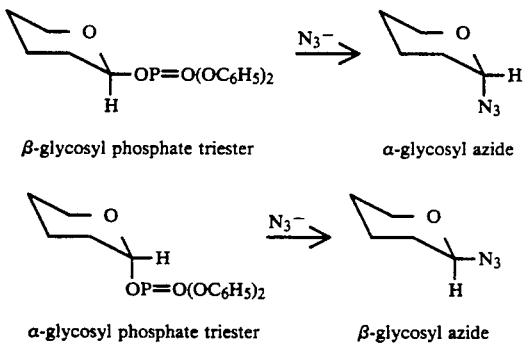

β-glycosyl phosphate triester     α-glycosyl azide

α-glycosyl phosphate triester     β-glycosyl azide

The reaction proceeds with a wide variety of glycosyl phosphate triesters as previously detailed in Formulae I and II. For example, α-phosphate triesters of protected glucopyranose, galactopyranose, 2-acetamido-2-deoxy-glucopyranose and fucopyranose all yield, exclusively, the corresponding β-glycosyl azide under the reaction conditions of the process of the present invention. In addition, β-phosphate triesters of derivatives of mannopyranose and rhamnopyranose yield, exclusively, the corresponding α-glycosyl azide under the reaction conditions of the process of the present invention. However, the scope of the process of the present invention is not limited to the described glycosyl phosphate triesters but is expected to operate on any glycosyl phosphate triester provided that the glycosyl phosphate group (either axial or equitorial) is cis to the adjacent C-2 substituent.

In the process of the present invention suitable sources of an azide ion for reaction with the glycosyl phosphate triester are metal azides, in particular alkali metal azides. Preferred are sodium azide or potassium azide.

The reaction is conducted in a polar, aprotic solvent in a dry inert atmosphere such as argon or nitrogen. Examples of suitable solvents include, but are not limited to, dimethylformamide, dimethylacetamide, dimethylsulfoxide, dimethylcarbonate, or N-methylpyrrolidone. The reaction time is typically from about 2 to about 20 hours. Vigorous agitation of the reaction mixture is required.

The mole ratio of glycosyl phosphate triester to metal azide suitable for use in the process of the present invention is from about 1:1 to about 1:100. Preferred for use herein is a mole ratio of about 1:10. Use of mole ratios in excess of about 1:10 are operable, but constitute a waste of reagent.

The process of the present invention is conducted at a temperature of from about $40°$ C. to about $80°$ C., preferably from about $50°$ C. to about $70°$ C. The displacement of the phosphate group by the azide ion is faster and temperatures of about $50°$ C. to about $70°$ C. are sufficient for the displacement reaction to proceed when the glycosyl phosphate triester utilized as substrate has benzyl protecting groups; whereas, longer reaction times and higher reaction temperatures of about $70°$ C. to about $80°$ C. are required for the displacement reaction to proceed when the glycosyl phosphate triester utilized as substrate has benzoate protecting groups.

Isolation of the desired product is achieved by means common in the art. For example, the desired product can be isolated by high pressure liquid chromatography or column chromatography. Exemplary details are provided hereinafter in the examples.

Glycosyl azides can also be prepared by reacting a glycosyl phosphate triester with a Lewis acid catalyst such as trimethylsilyl triflate, and trimethylsilyl azide to yield the corresponding glycosyl azide. However, the reaction yields an anomeric mixture of glycosyl azides. For example, under these reaction conditions α-phosphate triesters of derivatives of glucopyranose and galactopyranose, and β-phosphate triesters of derivatives of mannopyranose and rhamnopyranose yield the corresponding glycosyl azide as a mixture of anomers.

EXAMPLES

The following examples illustrate the process of the present invention, but are not intended to limit it in any manner. All the reagents were purchased from Aldrich Chemical Co., Milwaukee, Wis. Thin layer chromatography of the reaction mixture to monitor the progress of the reaction can be performed on precoated plates of Silica Gel 60 $F_{254}$ (EM Science, Gibbstown, N.J.), and the spots were visualized with a spray containing 5% sulfuric acid in ethanol followed by heating. Column chromatography was done on silica gel 60 (230–400 mesh, EM Science). $^1$H NMR spectra were recorded at 300 MHz (GE NMR QE-300) and the $^{13}$C- NMR spectra was recorded at 75.0 and MHz with the same instrument. The hydrogen and carbon chemical shifts in deuterated chloroform, $CDCl_3$, are expressed relative to tetramethylsilane.

EXAMPLE 1

2,3,4,6-Tetra-O-acetyl-β-D-glucopyranosyl azide a) 2,3,4 6-Tetra-O-acetyl-D-glucopyranose A solution of acetobromoglucose (75.0g) in acetone (150 mL) was added to a vigorously stirred suspension of silver carbonate (35.0g) in 50% aqueous acetone (340 mL) over a period of 90 min. After 30 min. the solution was filtered over a pad of diatomaceous earth and the filtrate was evaporated to near dryness. The residue was then dissolved in dichloromethane and the organic layer was successively washed with water, ice-cold 0.5 M hydrochloric acid and saturated sodium bicarbonate solution. After being dried over anhydrous magnesium sulfate, the solution was evaporated to a dry residue, which was recrystallized (33.1g) from benzene. The mother liquor upon evaporation afforded an amorphous material (29.7g). $^1$H NMR in CDCl3 indicated the crystals to be 5:2 mixture of $\beta$ and $\alpha$ anomers and the foam from the mother liquor to be 1:1 anomeric mixture.

b) Diphenyl (2,3,4,6-tetra-O-acetyl-$\alpha$-D-glucopyranosyl)phosphate

A solution of 2,3,4,6-tetra-O-acetyl-D-glucopyranose (2.0g) in dichloromethane (40 mL) containing 4-N,N-dimethylaminopyridine (1.64g) was stirred at room temperature for 15 min. and then cooled to $-10°$ C. Diphenylchlorophosphate (2.8 mL) was added in drops and the solution was stirred between $-10°$ C. to $0°$ C. for 2 hr. and at 4° C. for 1 hr. The reaction mixture was then diluted with dichloromethane and the organic layer was washed with ice cold water, ice cold 0.5M hydrochloric acid and saturated solution of sodium bicarbonate. Chromatographic purification using ethyl acetate - hexane (2:3) afforded the title compound as a syrup, 2.6g. The structure was confirmed by $^1$H NMR.

c) 2,3,4,6-Tetra-O-acetyl-$\beta$-D-glucopyranosyl azide

A solution of diphenyl(2,3,4,6-tetra-O-acetyl-$\alpha$-D-glucopyranosyl)-phosphate (2.3g) in anhydrous dimethylformamide (100 mL) containing sodium azide (2.0g) was heated to 50° C. for 2 h. and to 70° C. for 1 h. TLC indicated that all the starting material disappeared and only one product was formed. The reaction mixture was evaporated to dryness and the residue was extracted with dichloromethane. This was then washed with water and then with saturated sodium bicarbonate solution. Evaporation of the solvent afforded a colorless syrup (1.5g) of the titled compound. As evidenced from the $^1$H NMR spectrum, the crude product was sufficiently pure to require no chromatographic purification for further use.

EXAMPLE 2

2,3,4,6-Tetra-O-benzoyl-$\beta$-D-glucopyranosyl azide a) Diphenyl (2,3,4,6-tetra-O-benzoyl-$\alpha$-D-glucopyranosyl)phosphate A solution of 2,3,4,6-tetra-O-benzoyl-D-glucopyranose (prepared by hydrolysis of the corresponding 1-bromide, 3.0g as described in Hewit, G., Fletcher, Jr., Methods in Carbohydrate Chemistry, Wolfram, M. L.; Whistler, R. L., Eds.; Vol. II, p. 226, Academic Press, New York, N.Y. (1963), herein incorporated by reference), in dichloromethane (40 mL) was cooled to $-15°$ C., and 4-N,N-dimethylaminopyridine (2.4g) and diphenyl chlorophosphate (4.2 mL) were added. The solution was stirred between $-15°$ C. to -31 10° C. for 2 hr. The reaction could not be followed by thin layer chromatography as the $\alpha$-phosphate triester product had nearly the same mobility as the starting material. Work up of the reaction mixture, followed by chromatographic purification (ethyl acetate—hexane=3:8) gave pure ($\alpha$-phosphate triester (2.5g) along with some impure product (971 mg). The $^1$H NMR was consistent with the structure expected for the title compound.

b) 2,3,4,6-Tetra-O-benzoyl-$\beta$-D-glycopyranosyl azide A solution of diphenyl(2,3,4,5-tetra-O-benzoyl-$\alpha$-D-glucopyranosyl)-phosphate (0.62g) in anhydrous dimethylformamide (20 mL) containing sodium azide (0.5g) was heated to 50° C. for 2 h and at 70° C. for 1 h and processed as described in Example 1. As evidenced from the $^1$H NMR spectrum, the crude product was sufficiently pure and did not require chromatographic purification.

EXAMPLE 3

2,3,4,6-Tetra-O-acetyl-$\beta$-D-galactopyranosyl azide a) 2,3,4,6-Tetra-O-acetyl-D-galactopyranose Acetobromogalactose (15.0g) was hydrolyzed according to the procedure described for Example 1$a$). The product was crystallized (5.4g) from benzene. The anomeric composition of the crystal was estimated by $^1$H NMR to be 5:2 in favor of $\beta$ anomer. The weight of the product from the mother liquor was 4.0g.

b) Diphenyl (2,3,4,6-tetra-O-acetyl-$\alpha$-D-galactopyranosyl)phosphate 2,3,4,6-Tetra-O-acetyl-D-galactopyranose (3.0g, recrystallized from benzene) was converted to the title compound as described in Example 1$b$). The yield of the product was 3.9g. $^1$H NMR (CDCl3).

c) 2,3,4,6-Tetra-O-acetyl-$\beta$-D-galactopyranosyl azide.

A solution of diphenyl(2,3,4,6-tetra-O-acetyl-$\alpha$-D-galactopyranosyl)-phosphate (2.94g) in anhydrous dimethylformamide (30 mL) containing sodium azide (2.2g) was heated to 50° C. for 24 h. and processed as described in Example 1. The product was purified by chromatography on a column of silica gel using ethyl acetate - hexane (3:8) as eluant to obtain the title compound (1.49g).

EXAMPLE 4

2-Acetamido-2-deoxy-3,4,6-tri-O-acetyl-$\beta$-D-glucopyranosyl azide a) 2-Acetamido-2deoxy-3,4,6-tri-O-acetyl-D-glucopyranose A solution of 2-acetamido-2-deoxy-3,4,6-tri-O-acetyl-$\alpha$-D-glucopyranosyl chloride [31.0g; prepared according to Horton, Org. Synthesis, 46, 1 (1966) herein incorporated by reference]; the crystallized product was contaminated to about 5-10% with 2-acetamido-2-deoxy-1,3,4,6-tetra-O-acetyl-$\alpha$-D-glucopyranose) in acetonitrile (125 mL) was added to a suspension of silver carbonate (30.0g) in 50% aqueous acetonitrile (220 mL) over a period of 15 min. and the reaction was continued at room temperature for 16 hr. The reaction mixture was filtered over a pad of Celite and the solution was evaporated to a volume of 150 mL. The solution was filtered again over a pad of Celite and the residue was washed with water (50 mL). The filtrate was extracted with methylene chloride (3×75 mL, most of the desired product remained in the aqueous layer). The organic layer was repeatedly extracted with water (6×100 mL) and all the aqueous solutions were combined. Thin layer chromatography examination of the aqueous layer showed the presence of a homogeneous product, whereas the organic layer contained traces of the title compound and the peracetylated material that was present in the starting material. The aqueous layer was evaporated to dryness, the residue redissolved in dichloromethane, then dried over anhydrous magnesium sulfate and evaporated to obtain an amorphous product (24.0g). Examination by $^1$H NMR confirmed the structure of the product to be the titled compound containing greater than 90% of the α-anomer.

b) Diphenyl (2-acetamido-2-deoxy-3,4,6-tri-O-acetyl-α-D-glycopyranosyl)-phosphate To a solution of 2-acetamido-2-deoxy-3,4,6-tri-O-acetyl-D-glucopyranose (Example 6a, 5.0g) in dichloromethane (400 mL) at −30° C. containing 4-N,N-dimethylaminopyridine (15.0g), diphenyl chloro-phosphate (20.0 mL) was added and the reaction mixture was stirred between −30° to −25° C. for 2 hr. Examination of the reaction mixture showed a single major product (the title compound) along with traces of a minor product. The reaction mixture was worked up as described above in Example 1b) and purified by chromatography using ethyl acetate - hexane (3:2) as eluant. The yield of the amorphous material was 5.2g.

c) 2Acetamido-2-deoxy-3,4,6-tri-O-acetyl-β-D-glucopyranosyl azide

A solution of diphenyl(2-acetamido-2-deoxy-3,4,6-tri-O-acetyl-6O-D-glucopyranosyl)phosphate (0.7g) in anhydrous dimethylformamide (20 mL) containing sodium azide (0.5g) was heated to 50° C. for 1 h. and processed as described in Example 1c). $^1$H NMR indicated the crude product (0.46g) contained essentially the title compound only.

EXAMPLE 5

2,3,4-Tri-O-acetyl-α-L-rhamnopyroanosyl azide a) 2,3,4-Tri-O-acetyl-L-rhamnopyranose

L-Rhamnose (46.0g) was acetylated with acetic anhydride in pyridine and the crude acetate obtained was treated with 30% hydrogen bromide in acetic acid. The crude bromide was hydrolyzed as described in the procedure of Example 1a). Following hydrolysis and filtration over diatomaceous earth, the filtrate was concentrated during which crystals started to appear. These were filtered and washed with ice cold water (the title compound was found to be appreciably soluble in water) to obtain 17.0g of solid (residue 1). The filtrate was extracted with dichloromethane and the dichloromethane layer was washed with ice-cold hydrochloric acid and saturated sodium bicarbonate solution. Evaporation of the solvent afforded 32.0g of solid (residue 2). $^1$H NMR of residues 1 and 2 indicated to be an anomeric mixture with greater than 75% α anomer.

b) Diphenyl (2,3,4-tri-O-acetyl-β-L-rhamnopyranosyl)phosphate

To a solution of 2,3,4-tri-O-acetyl-L-rhamnopyranose (3.0g) in dichloromethane (50 mL), a solution of 4-N,N-dimethylaminopyridine (2.4g) and diphenyl chlorophosphate (4.2 mL) in dichloromethane (20 mL) was added at room temperature over a period of 60 min. After 2 hr., the reaction mixture was worked up and purified by chromatography using ethyl acetate/hexane (3:8) as eluant. After elution of the α-phosphate triester, the eluant was changed to ethyl acetate/hexane (2:3) to obtain the β-phosphate. The yield of the purified product was 3.5g. The structure was confirmed by NMR.

c) 2,3,4-Tri-O-acetyl-α-L-rhamnopyranosyl azide

A solution of diphenyl(2,3,4-tri-O-acetyl-β-L-rhamno-pyranosyl)-phosphate (0.54g) in anhydrous dimethylformamide (20 mL) containing sodium azide (0.5g) was heated to 70° C. for 3 h. and processed as described in Example 1c). The product was purified by chromatography on a column of silica gel using ethyl acetate - hexane (1:4) as eluant to obtain the title compound (0.31g)

EXAMPLE 6

2,3,4-Tri-O-acetyl-β-D-fucopyranosyl azide a) 2,3,4-Tri-O-acetyl-L-fucopyranose

L-Fucose (46.0g) was converted to 2,3,4-tri-O-acetyl-L-fucopyranose according to the procedure described in Example 5a) for 2,3,4-tri-O-acetyl-L-rhamnopyranose. The crude syrupy product contained about 10% of the furanose derivative in addition to the pyranose (α anomer about 48%, β anomer about 41%). Upon standing in the refrigerator, pure pyranose crystallized out, which was washed with ice-cold ethanol-hexane to give colorless crystals (20.5g). $^1$H NMR showed the crystals to be greater than 90% of the α anomer.

b) Diphenyl(2,3,4-tri-O-acetyl-α-D-fucopyranosyl)-phosphate 2,3,4-Tri-O-acetyl-L-fucopyranose (2.0g) was converted to the phosphate triester according to the procedure described in Example 3b). The yield of product was 2.0g and the structure was confirmed by NMR.

c) 2,3,4-Tri-O-acetyl-β-D-fucopyranosyl azide

A solution of diphenyl(2,3,4-tri-O-acetyl-α-D-fucopyranosyl)-phosphate (2.0g) in anhydrous dimethylformamide (80 mL) containing sodium azide (2.0g) was heated to 50° C. for 2 h. and processed as described in Example 1c). The product was purified by chromatography on a column of silica gel using ethyl acetate - hexane (3:8) as eluant to obtain the title compound (1.13g ).

TABLE 1

| | | NMR PARAMETERS OF VARIOUS HEXOPYRANOSYL AZIDES | | | | | |
|---|---|---|---|---|---|---|---|
| Ex. | | 1 | 2 | 3 | 4 | 5 | 6 |
| 1 | $^1$H | 4.65 | 4.96 | 5.23 | 5.12 | 3.80 | 4.29 |
| 2 | $^1$H | 4.98 | 5.50 | 5.94 | 5.73 | 4.27 | 4.60 |
| 3 | $^1$H | 4.59 | 5.16 | 5.03 | 5.42 | 4.01 | 4.19 |
| | $^{13}$C | 88.4 | 68.4 | 70.9 | 67.1 | 73.1 | 61.3 |
| 4 | $^1$H | 4.75 | 3.92 | 5.25 | 5.11 | 3.79 | 4.29 |
| | $^{13}$C | 88.5 | 54.5 | 72.4 | 68.6 | 74.2 | 62.1 |
| 5 | $^1$H | 5.30 | 5.13 | 5.19 | 5.07 | 4.02 | 1.27 |
| | $^{13}$C | 87.7 | 68.5 | 69.7 | 68.8 | 70.7 | 17.5 |
| 6 | $^1$H | 4.58 | 5.14 | 5.03 | 5.27 | 3.90 | 1.25 |
| | $^{13}$C | 88.3 | 70.2 | 71.3 | 68.6 | 71.7 | 16.0 |

What is claimed is:

1. A process for the stereospecific preparation of a glycosyl azide of Formula III or IV

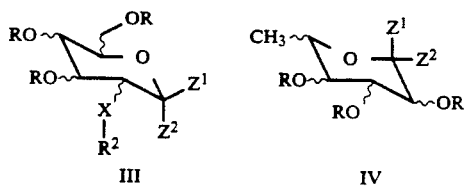

wherein:
R is alkyl, aryl, aralkyl, acyl or aroyl;
X is oxygen or NH; when X is oxygen, $R^2$ is alkyl, aryl, aralkyl, acyl or aroyl; when X is NH, $R^2$ is acyl, aroyl, or alkylcarbamyl; and
one of $Z^1$ or $Z^2$ is $N_3$, and the other is H;
comprising reacting a metal azide with a glycosyl phosphate triester having the phosphate group cis to the adjacent C-2 substituent at a temperature of from about 40 degrees Centigrade to about 80 degrees Centigrade wherein the glycosyl phosphate triester is a compound of Formula I or II

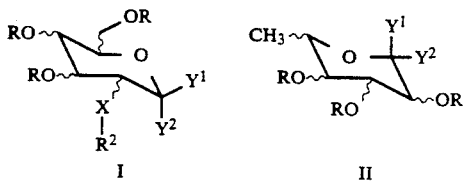

wherein:
R is alkyl, aryl, aralkyl, acyl or aroyl;
X is oxygen or NH; when X is oxygen $R^2$ is alkyl, aryl, aralkyl, acyl or aroyl, when X is NH, $R^2$ is acyl, aroyl, or alkylcarbamyl;
one of $Y^1$ or $Y^2$ is O—P↑O(OR$^4$)$_2$
and the other is H; and
$R^4$ is aryl and wherein the reaction is carried out in the presence of a polar, aprotic solvent.

2. The process of claim 1 wherein for Formula III or IV:
R is benzyl, acetyl or benzoyl;
When X is oxygen, $R^2$ is benzyl, acetyl or benzoyl;
When X is —NH, $R^2$ is acetyl;
one of $Z^1$ or $Z^2$ is $N_3$, and the other is hydrogen.

3. The process of claim 1 wherein for Formula I or II:
R is benzyl, acetyl or benzoyl;
When X is oxygen, $R^2$ is benzyl, acetyl, or benzoyl;
When X is —NH, $R^2$ is acetyl;
one of $Y^1$ or $Y^2$ is

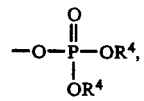

and the other is H; and
$R^4$ is phenyl.

4. The process of claim 1 wherein the metal azide is an alkali metal azide.

5. The process of claim 4 wherein the metal azide is sodium azide or potassium azide.

6. The process of claim 1 conducted at a temperature of from about 50° C. to about 70° C.

7. The process of claim 1 wherein the solvent is selected from the group consisting of dimethylformamide, dimethylacetamide, dimethylsulfoxide, dimethylcarbonate, and N-methylpyrrolidone.

8. The process of claim 1 wherein the mole ratio of glycosyl phosphate triester to metal azide is from about 1:1 to about 1:10.

9. The process of claim 1 conducted in a dry inert atmosphere of nitrogen or argon.

10. The process of claim 1 conducted with vigorous agitation.

* * * * *